US008198328B2

(12) United States Patent
Brooks et al.

(10) Patent No.: US 8,198,328 B2
(45) Date of Patent: Jun. 12, 2012

(54) TREATMENT OF CANCER USING BENZOIC ACID DERIVATIVES

(75) Inventors: Peter C. Brooks, Carmel, NY (US); Danielle Morais, Bedford Hills, NY (US); Leonard Liebes, New York, NY (US); Dorothy Rodriguez, Rowland Hts., CA (US)

(73) Assignee: New York University, New York, NY (US)

( * ) Notice: Subject to any disclaimer, the term of this patent is extended or adjusted under 35 U.S.C. 154(b) by 1488 days.

(21) Appl. No.: 11/040,611

(22) Filed: Jan. 19, 2005

(65) Prior Publication Data

US 2005/0209334 A1    Sep. 22, 2005

Related U.S. Application Data

(60) Provisional application No. 60/538,360, filed on Jan. 21, 2004.

(51) Int. Cl.
*A61K 31/195* (2006.01)
(52) U.S. Cl. ........................................ 514/567
(58) Field of Classification Search .................. None
See application file for complete search history.

(56) References Cited

U.S. PATENT DOCUMENTS

| | | | |
|---|---|---|---|
| 3,836,571 A | 9/1974 | Skoultchi et al. | |
| 4,535,183 A | 8/1985 | Kneen | |
| 5,773,460 A | 6/1998 | Gaboury et al. | |
| 5,958,980 A | 9/1999 | Rhodes | |
| 6,294,695 B1 * | 9/2001 | Bekesi et al. | 564/161 |
| 6,368,598 B1 * | 4/2002 | D'Amico et al. | 424/181.1 |
| 6,395,720 B1 | 5/2002 | Kreutz | |
| 6,514,506 B1 * | 2/2003 | Mammone et al. | 424/401 |
| 6,667,299 B1 * | 12/2003 | Ahlem et al. | 514/178 |
| 6,740,777 B2 | 5/2004 | Tsukamoto et al. | |
| 6,825,233 B2 | 11/2004 | Ericsson et al. | |
| 6,867,238 B2 * | 3/2005 | Schrauzer | 514/706 |
| 7,691,905 B2 | 4/2010 | Brooks et al. | |
| 7,705,049 B2 | 4/2010 | Brooks et al. | |
| 2001/0044431 A1 * | 11/2001 | Rodriguez | 514/179 |
| 2002/0049186 A1 | 4/2002 | Ekwuribe et al. | |
| 2003/0082552 A1 * | 5/2003 | Wolffe et al. | 435/6 |
| 2003/0091518 A1 * | 5/2003 | Pauly et al. | 424/59 |
| 2003/0104519 A1 * | 6/2003 | Evans | 435/69.1 |
| 2003/0194696 A1 * | 10/2003 | Zauderer et al. | 435/5 |

FOREIGN PATENT DOCUMENTS

| | | |
|---|---|---|
| CA | 2191850 | 10/1996 |
| CA | 2367963 A1 | 9/2000 |
| CA | 2448089 A1 | 12/2002 |
| CA | 2472578 A1 | 7/2003 |
| DE | 19505518 | 8/1996 |
| EP | 3663 A2 | 8/1979 |
| GB | 1267064 | 3/1972 |
| JP | 60224619 | 11/1985 |
| WO | 96/19243 | 6/1996 |
| WO | 03/061566 | 7/2003 |
| WO | WO 03/061566 * | 7/2003 |
| WO | 2004/058241 | 7/2004 |
| WO | WO 2004/025241 A1 | 7/2004 |
| WO | WO 2005/070043 A2 | 8/2005 |

OTHER PUBLICATIONS

Moore et al. (Pregnane X Receptor (PXR), Constitutive Androstane Receptor (CAR), and Bezoate X Receptor (BXR) Define Three Pharmacologically Distinct Classes of Nuclear Receptors; Molecular Endocrinology 16(5):977-986).*
Winter, "Organic Chemistry I for Dummies", Wiley Publishing Inc., p. 47 (2005).*
Kliewer, Steven A., et al., "An Orphan Nuclear Receptor Activated by Pregnanes Defines a Novel Steroid Signaling Pathway", Cell, Jan. 9, 1998, vol. 92, pp. 73-82.
Takeshita, Akira, et al., "Putative Role of the Orphan Nuclear Receptor SXR (Steroid and Xenobiotic Receptor) in the Mechanism of CYP3A4 Inhibition by Xenobiotics", The Journal of Biological Chemistry, Sep. 6, 2002, vol. 277, No. 36, pp. 32453-32458.
Moore, Linda B., et al., "Pregnane X Receptor (PXR), Constitutive Androstane Receptor (CAR), and Benzoate X Receptor (BXR) Define Three Pharmacologically Distinct Classes of Nuclear Receptors", Molecular Endrocrinology, May 2002, vol. 16, No. 5, pp. 977-986.
Kraakman-Van Der Zwet, Maria, et al., "Brca2 (XRCC11) Deficiency Results in Radioresistant DNA Synthesis and a Higher Frequency of Spontaneous Deletions", Molecular and Cellular Biology, Jan. 2002, vol. 22, No. 2, pp. 669-679.
Wong, Johnson M.S., et al., "Interaction between BRCA2 and replication protein A is compromised by a cancer-predisposing mutation in BRCA2", Oncogene, 2003, vol. 22, pp. 28-33.
Blumberg, Bruce, et al., "SXR, a novel steroid and xenobiotic-sensing nuclear receptor", Genes & Development, Oct. 15, 1998, vol. 12, No. 20, pp. 3195-3205.
Database CAPLUS on STN (Columbus, OH USA) No. 93:114154 'amino-substitued phenyl and heteroaryl compounds and pharmaceutical compositions containing them' abstract, Shepherd, see RN 53624-18-3.
International Search Report for PCT/US05/02402 issued Nov. 30, 2005.
Bedikian, Agop Y., et al. 2004. Phase II evaluation of paclitaxel by short intravenous infusion in metastatic melonoma. *Melanoma Research* 14(1):66-66 (abstract only).

(Continued)

*Primary Examiner* — David J Blanchard
*Assistant Examiner* — Barbara Frazier
(74) *Attorney, Agent, or Firm* — Fish & Richardson P.C.

(57) ABSTRACT

The present invention provides a method of treating cancer using benzoic acid derivatives, alone or in combination with standard treatments such as chemotherapy and radiotherapy. Also provided are methods of screening for benzoic derivatives based on their ability to inhibit the enzyme tyrosinase or to bind to and activate PXR/SXR xenobiotic receptors.

7 Claims, 8 Drawing Sheets

OTHER PUBLICATIONS

Buccheri, G., and D. Ferrigno. 2004. Second-line weekly paclitaxel in pateints with inoperable non-small cell lung cancer who fail combination chemotherapy with cisplatin. *Lung Cancer* 45(2):227-36 (abstract only).
Bristol-Myers Squibb Company. 2007. Taxol (paclitaxel) Injection (Patient Information Included).
U.S. Appl. No. 61/276,421, filed Sep. 10, 2009.
Wang, Ming-zhen et al., Shaanxi Shifan Daxue Xuebao, Ziran Kexueban (2002), 30(1), 78-82, (Abstract).
Dominikiewicz et al., Archiwum Chemji i Farmacji (1939), 4, 8-21, (Translation).
Graphical Representation Standards for Chemical Structure Diagrams (IUPAC Recommendations 2008), 80 Pure Appl. Chem. 277-410 (2008).

* cited by examiner

TREATMENT OF CANCER USING BENZOIC ACID DERIVATIVES

This application claims priority under 35 U.S.C. §119(e) to U.S. provisional application No. 60/538,360, filed Jan. 21, 2004; the contents of which are hereby incorporated by reference in their entirety.

GOVERNMENT SUPPORT

This work was supported in part by NIH grant No. ROICA91645. Pursuant to the terms of that grant, the federal government may have certain rights to this invention.

FIELD OF THE INVENTION

The present invention relates to the treatment of cancer using derivatives of p-amino-benzoic acid (PABA). The invention also relates to the potentiation of radiotherapy, chemotherapy, or a combination thereof, with PABA derivatives that are agonists of the PXR/SXR xenobiotic receptor. The present invention further relates to a method of screening to identify lead compounds that agonize the PXR/SXR receptor.

BACKGROUND OF THE INVENTION

Cancer

Cancer accounts for nearly one-quarter of deaths in the United States, exceeded only by heart disease. In the year 2000, there were 553,091 cancer deaths in the US. In 2003, the American Cancer Society estimates that this number will increase to approximately 556,500, due to aging and growth of the population. Lung cancer is the most common fatal cancer in men (31%), followed by prostate (10%), and colon & rectum (10%). In women, lung (25%), breast (15%), and colon & rectum (11%) are the leading sites of cancer death. Among children, leukemia is the most common cancer among children ages 0-14 years and it comprises approximately 30% of all childhood cancers and accounts for the most childhood deaths. Acute lymphocytic cancer is the most common form of leukemia in children. It is estimated that 1.33 million new cases of cancer were diagnosed in 2003 (American Cancer Society, 2003 Cancer Statistics Slide Set 2003).

Melanoma. Studies have indicated that nearly 45,000 new cases of melanoma are diagnosed each year in the U.S. and approximately 20% of patients will die of metastatic disease. Melanomas arise from the malignant conversion of melanocytes, which in turn are derived from mesenchymal neural crest cells. Melanomas undergo melanogenesis, a complex process that results in the production of melanin. Melanogenesis is initiated by the hydroxylation of L-tyrosine, to form L-dihydroxyphenylalanine (L-DOPA), which is then converted to DOPAchrome by specific melanocyte-associated enzymes, including tyrosinase. A further series of oxidation and reduction reactions ultimately convert DOPAchrome to melanin. It has been suggested that melanogenesis may account for the resistance of melanomas to treatment with ionizing radiation and chemotherapy. It has also been suggested that byproducts of melanogenesis are responsible for other adverse effects including immunosuppression, fibrosis and mutagenesis.

Current Treatments

Chemotherapy (CT) and radiation therapy (RT), and combinations thereof, remain the leading defenses against cancer, although recent advances in the field have led to widespread uses of specialized treatments such as angiogenesis inhibitors, biological therapies, including adjuvant therapy to boost the patient's immune system, antibody therapy, vaccine therapy, and photodynamic therapy.

In addition to numerous adverse effects of RT and CT, a major limiting factor is the development of drug resistance by the tumors, and induction of tumor cell growth arrest and senescence. While senescent tumors do not increase in size per se, they still retain the capacity to produce and secrete tumor stimulating mitogens and pro-angiogenic factors that can lead to tumor progression.

The present inventors have previously unexpectedly shown that PABA, which inhibits tyrosinase and melanogenesis, in addition to being a therapeutic for melanotic tumors, can also potentiate treatment of non-melanotic carcinomas with RT and CT (see co-pending U.S. Provisional Application Ser. No. 60/538,359 filed Jan. 21, 2004. Accordingly, it was hypothesized that benzoic acid derivatives that also inhibit tyrosinase may also have this activity for both melanotic and non-melanotic cancer.

Cell Cycle Regulation and PXR/SXR Receptors

Induction of cell-cycle arrest and by activation of G1/S and G2/M check points is known to be critical for the capacity of the cell to undergo DNA repair prior to re-entering the cell-cycle. Moreover, studies have provided that overriding the cell cycle check point controls in cells with DNA damage (e.g., induced by RT or CT), can force the cell to re-enter the cell cycle without repairing the damage, leading to mitotic catastrophe and cell death by apoptosis.

Recent studies have shown that parameters such as the degree of oxygenation/hypoxia, the expression and function of DNA repair proteins, cell cycle and checkpoint control proteins, and cell adhesion and extracellular matrix proteins all regulate tumor radiosensitivity. In particular, in response to DNA-damaging agents such as RT and CT, several kinases are activated (e.g., ATM and ART) which phosphorylate check point control proteins such as Chk2, which in turn, phosphorylates CDC25A, targeting CDC25A for degradation. Degradation of CDC25A leads to cell cycle arrest and DNA repair, while overexpression of CDC25A has been demonstrated to activate Cdk2 kinase, leading to accumulation of Cyclin E/Cck2 complexes and cell cycle progression followed shortly by cell death. Studies have suggested that alteration of cell cycle regulators such as CDC25A, CHK-1 and CHK-2 can sensitize sells to death by RT and CT, suggesting that agents that inhibit cell cycle arrest or promote cell cycle transition may be useful as adjuvant therapy for RT or CT.

Induction of cell cycle DNA repair proteins in response to cell cycle arrest is also hypothesized to have a role in radio- and chemosensitivity. Studies have shown that BRCA-2, a DNA repair protein, can regulate transcription of RNA polymerase II, or directly bind to Replication Protein A to regulate DNA repair. Accordingly agents that functionally inactivate or decrease expression of BRCA-2 may enhance cell cycle progression, and hence, enhance sensitivity of tumor cells to CT and RT (Wong et al., Oncogene 2003; 22: 28-33; and Kraakman-van der Zwet et al., Mol. Cell Biol. 2002; 22: 669-679).

para-amino-benzoic acid (hereinafter "PABA"), is a water-soluble naturally-occurring compound that is essential for microorganisms and some animals, but not humans. PABA also has been shown to inhibit cell cycle arrest and DNA repair. Studies in *Xenopus* embryos have revealed a signaling pathway mediated by endogenous benzoic acid derivatives (i.e., PABA derivatives such as 3-hydroy ethyl benzoate or 3-HEB) and orphan nuclear hormone receptors, benzoate X receptors (BXR). BXR heterodimerizes with the orphan retinoic acid X receptors (RXR) to regulate gene expression. A human and rodent homologue of BXR has been identified and is designated Pregnane X receptor or steroid X receptor (PXR/SXR). PXR/SXR is a member of xenobiotic nuclear receptors which function in induction of cytochrome P450 enzymes involved in drug metabolism and detoxification of xenobiotic compounds, and have limited expression restricted to the liver and small intestine. PABA and PABA derivatives have been shown to bind and activate the PXR/SXR receptor (Moore et al., Mol. Endocrinol. 2002; 16: 977-986).

Interestingly, the PXR/SXR receptor has also been found to be abnormally expressed in some tumors, such as melanoma (see Moore, supra). The present invention demonstrates that PABA and PABA derivatives which bind to PXR/SXR can surprisingly potentiate tumoricidal effects of CT and RT in tumor cells overexpressing PXR/SXR, likely by inhibiting cell cycle arrest and DNA repair through transcriptional regulation of cell cycle regulatory proteins.

There remains a need in the art for therapies that inhibit cell cycle arrest and DNA repair, and hence, cell senescence specifically in tumor cells, in order to sensitize tumor cells to killing by RT and CT. Accordingly, it is likely that specific PXR/SXR agonists may provide a novel approach to enhance the anti-tumor effects of CT and RT in tumor cells and not normal cells.

SUMMARY OF THE INVENTION

The present invention provides a method of treating cancer, comprising administering an effective amount of a benzoic acid derivative.

In on embodiment, the benzoic acid derivative is administered as monotherapy.

In another embodiment, the benzoic acid derivative is administered in combination with chemotherapy or radiation therapy.

In a preferred embodiment, the benzoic acid derivative is the compound designated C-45, depicted in FIG. 1.

In a specific embodiment, the benzoic acid derivative inhibits the enzyme tyrosinase.

The present invention also provides a method for treating cancer comprising cells which express the PXR/SXR xenobiotic receptor, which method comprises administering a compound which is an agonist of the PXR/SXR receptor.

In one embodiment, the PXR/SXR agonist is a benzoic acid derivative.

In another embodiment, the PXR/SXR agonist is a compound that inhibits expression or activity of a DNA repair protein and increase expression or activity of a cell cycle progression protein.

The present invention further provides a method of screening for compounds which are agonists of the PXR/SXR receptor by i) contacting host cells containing a reporter gene construct regulated by a xenobiotic response element ii) contacting the host cells with a test compound, and iii) determining the increase in expression of the reporter gene compared to untreated cells harboring the xenobiotic response element.

DETAILED DESCRIPTION

It has now been surprisingly discovered that PABA and specific PABA derivatives which i) inhibit enzymes such as tyrosinase involved in melanogenesis, or ii) bind to PXR/SXR receptors to regulate genes involved in cell cycle progression, can specifically target tumor cells (including non-melanotic tumors) and potentiate tumoricidal activities of CT and RT in such tumor cells. Accordingly, identification of lead compounds with these activities will likely lead to improved tumor-specific treatment for numerous cancers including melanoma.

The present invention is, in part, based on the findings described in the Examples. As described in Examples 1, PABA and related derivatives which inhibit tyrosinase are shown to enhance tumor cell death mediated by chemotherapy and ionizing radiation both in vitro and in vivo. As described in Examples 4-6, benzoic acid derivatives, via agonist effects on nuclear xenobiotic receptor PXR/SXR, can mediate expression of several cell cycle proteins, thereby affecting cell cycle progression and enhancing apoptotic tumor cell death mediated by chemotherapy and ionizing radiation.

DEFINITIONS

"para-amino-benzoic-acid" (PABA) is commercially available from, e.g., Sigma-Aldrich Chemical Co., St. Louis, Mo.

"PABA derivatives" or "benzoic acid derivatives" refer to compounds chemically related to benzoic acid, including alkyl and acyl analogues, chlorobenzoic acids, aminobenzoic acids and nitrobenzoic acids, and salts and esters thereof.

In a specific embodiment, the compound is the compound designated C-45 having the following Formula I:

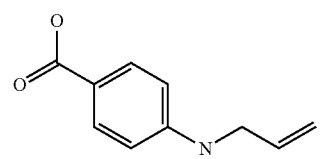

Figure 1:
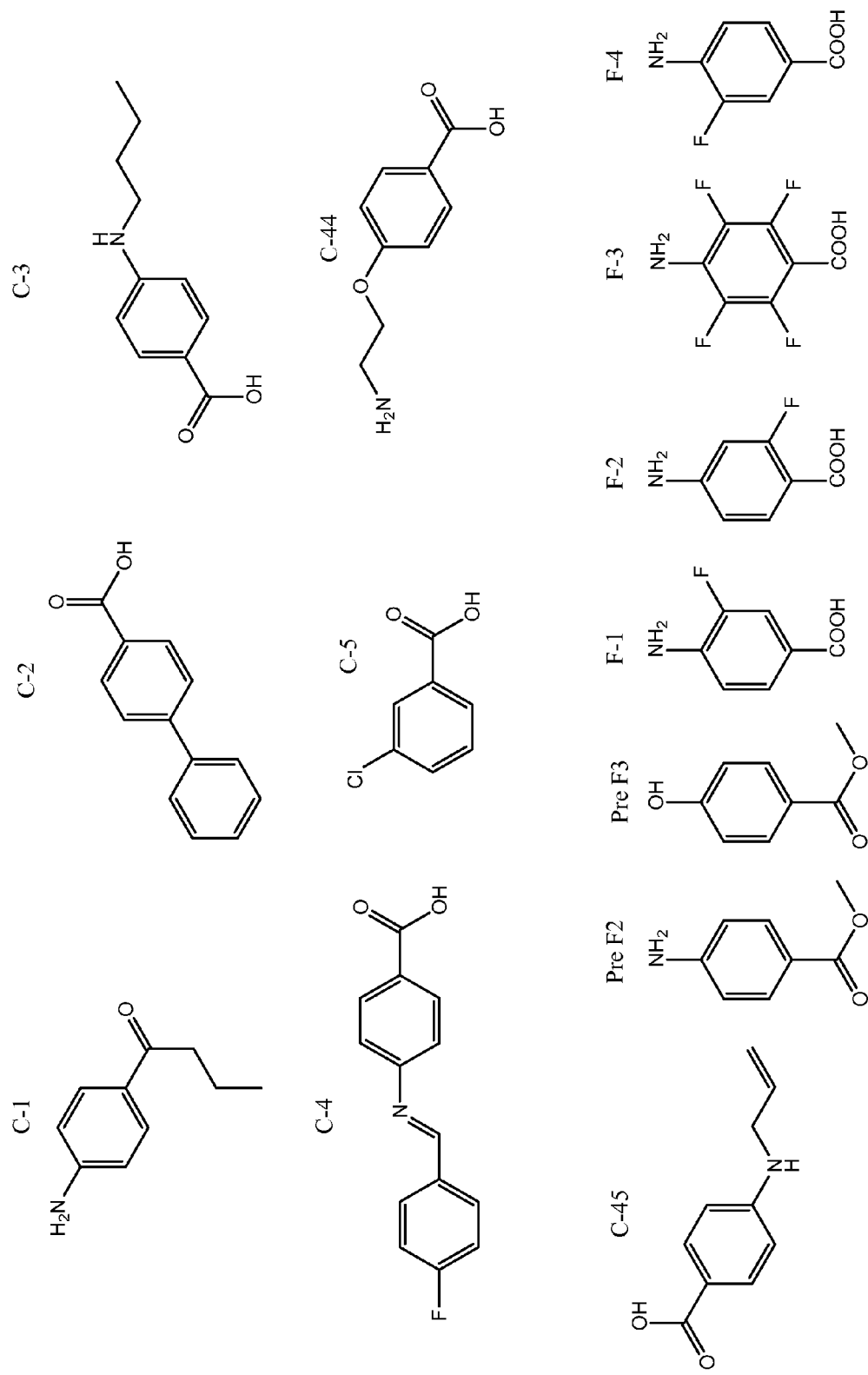
FIG. 1 depicts benzoic acid derivatives which can be used to treat cancer according to the method of the present invention.

Other specific derivatives contemplated for use in the present invention are depicted in FIG. 1.

Additional non-limiting benzoic acid derivatives included but are not limited to the following: 2-ethoxybenzoic acid, 3,4,5-trimethoxybenzoic acid methyl ester/methyl-3,4,5-trimethoxybenzoate, 3,4,5-trimethoxybenzoic acid, 3,5-dinitro-4-hydroxy benzoic acid (4-hydroxy-3,5-dinitrobenzoic acid), 3-acetoxy benzoic acid, 4-acetylbenzoic acid, 4-amino-2-chlorobenzoic acid, 4-chloro-3-sulfamoylbenzoic acid, 4-phenoxybenzoic acid, isovanillic acid, 2-bromo-5-fluorobenzonitrile, 5-bromo-2-iodobenzonitrile, 2,3,4,5,6-pentamethylbenzophenone, 3-nitrobenzophenone, 4,4'-dibromobenzophenone, 4-aminobenzophenone, 4-bromobenzophenone, 4-hydroxybenzophenone, 5-amino-2-nitrobenzotrifluoride, 2-amino-N-cyclohexyl-N-methylbenzylamine hydrochloride, 2-amino-N-cyclohexyl-n-methylbenzylamine, 2-(hydroxymethyl)-benzofuran, 2,3-dimethylbenzofuran, 2-acetyl-7-methoxybenzofuran, 2-acetylbenzofuran, 2-benzofurancarboxaldehyde, 2-benzofurancarboxylic acid, 2-benzofuranoyl chloride, 6,7-dihydro-4(5H)-benzofuranone, 2-methoxy-5-sulfamoylbenzoic acid, 4-(1H-imidazol-1-yl)-benzoic acid, 4-(chlorosulfonyl)-benzoic acid, 4-nitrobenzamide, 4-nitrobenzoyl chloride, 5-chloro-2-methoxybenzoic acid, 1,4-dihydro-2-methylbenzoic acid, 2,3,5-triiodobenzoic acid, 2,4,5-trimethoxybenzoic acid, 2,4-dichloro-5-sulfamoylbenzoic acid, 2,4-dimethoxybenzoic acid, and 2,5-dimethoxybenzoic acid.

"Cancer" refers to abnormal, malignant proliferations of cells originating from epithelial cell tissue (carcinomas), blood cells (leukemias, lymphomas, myelomas), connective tissue (sarcomas), or glial or supportive cells (gliomas). In one embodiment, the invention relates to the treatment of carcinomas and blood cell tumors. In a preferred embodiment, the invention relates to the treatment of lung tumors, breast tumors, ovarian tumors, pancreatic tumors, glioblastoma tumors, and sarcomas.

The term cancer includes but is not limited to the following: acute lymphoblastic leukemia, acute myeloid leukemia, adrenocortical carcinoma, carcinoma, aids-related cancers, aids-related lymphoma, anal cancer, astrocytoma (cerebellar), bile duct cancer (extrahepatic), bladder cancer, bone cancer (osteosarcoma/malignant fibrous histiocytoma), brain stem glioma, ependymoma, childhood visual pathway and hypothalamic glioma, breast cancer (including male), bronchial adenomas/carcinoids, carcinoid tumor (gastrointestinal), islet cell carcinoma, carcinoma of unknown primary origin, central nervous system lymphoma, cervical cancer, childhood cancers, chronic lymphocytic leukemia, chronic myelogenous leukemia, chronic myeloproliferative disorders, clear cell sarcoma of tendon sheaths, colon cancer, colorectal cancer, cutaneous T-cell lymphoma, endometrial cancer, ependymoma, ovarian epithelial cancer, esophageal cancer, Ewing's family of tumors, extracranial germ cell tumor, extragonadal germ cell tumor, intraocular melanoma, retinoblastoma, gallbladder cancer, gastric (stomach) cancer, germ cell tumor, ovarian germ cell tumor, gestational trophoblastic tumor, hairy cell leukemia, head and neck cancer, hepatocellular (liver) cancer, Hodgkin's lymphoma, hypopharyngeal cancer, Kaposi's sarcoma, kidney cancer, laryngeal cancer, lip and oral cavity cancer, liver cancer, lung cancer (non-small cell and small cell), lymphoma, macroglobulinemia, Waldenström's, malignant mesothelioma, medulloblastoma, melanoma, Merkel cell carcinoma, metastatic squamous neck cancer with occult primary, multiple endocrine neoplasia syndrome, multiple myeloma/plasma cell neoplasm, mycosis fungoides, myelodysplastic syndromes, myelodysplastic/myeloproliferative diseases, multiple myeloma, chronic myeloproliferative disorders, nasal cavity and paranasal sinus cancer, nasopharyngeal cancer, neuroblastoma, oral cancer, oral cavity and lip cancer, oropharyngeal cancer, ovarian low malignant potential tumor, pancreatic cancer, paranasal sinus and nasal cavity cancer, parathyroid cancer, penile cancer, pheochromocytoma, pineal and supratentorial primitive neuroectodermal tumors, pituitary tumor, pleuropulmonary blastoma, prostate cancer, rectal cancer, renal cell (kidney) cancer, renal pelvis and ureter, transitional cell cancer, rhabdomyosarcoma, salivary gland cancer, soft tissue sarcoma, Sezary syndrome, skin cancer (non-melanotic), small intestine cancer, supratentorial primitive neuroectodermal tumors, T-cell lymphoma, cutaneous testicular cancer, thymoma, thymic carcinoma, thyroid cancer, urethral-cancer, endometrial uterine cancer, uterine sarcoma, vaginal cancer, vulvar cancer, and Wilm's tumor.

The term also includes childhood cancers of all or any of the above-identified cancers.

In a specific embodiment, the cancer is melanoma.

The term "radiation therapy" or "radiotherapy" refers to use of high-energy radiation to treat cancer. Radiation therapy includes externally administered radiation, e.g., external beam radiation therapy from a linear accelerator, and brachytherapy, in which the source of irradiation is placed close to the surface of the body or within a body cavity. Common radioisotopes used include but are not limited to cesium ($^{137}$Cs), cobalt ($^{60}$Co), iodine ($^{131}$I), phosphorus-32 ($^{32}$P), gold-198 ($^{198}$Au), iridium-192 ($^{192}$Ir), yttrium-90 ($^{90}$Y), and palladium-109 ($^{109}$Pd). Radiation is generally measured in Gray units (Gy), where 1 Gy=100 rads.

"Chemotherapy" (CT) refers to treatment with anti-cancer drugs. The term encompasses numerous classes of agents including platinum-based drugs, alkylating agents, anti-metabolites, anti-miotic agents, anti-microtubule agents, plant alkaloids, and anti-tumor antibiotics, kinase inhibitors, proetasome inhibitors, EGFR inhibitors, HER dimerization inhibitors, VEGF inhibitors, and antisense molecules, and includes antibodies. Such drugs include but are not limited to adriamycin, melphalan, ara-C, BiCNU, busulfan, CCNU, pentostatin, the platinum-based drugs carboplatin, cisplatin and oxaliplatin, cyclophosphamide, daunorubicin, epirubicin, dacarbazine, 5-fluorouracil (5-FU), fludarabine, hydroxyurea, idarubicin, ifosfamide, methotrexate, altretamine, mithramycin, mitomycin, bleomycin, chlorambucil, mitoxantrone, nitrogen mustard, mercaptopurine, mitozantrone, paclitaxel (TAXOL®), vinblastine, vincristine, vindesine, etoposide, gemcitabine, monoclonal antibodies such as Herceptin®, Rituxan®, Campath®, Zevelin® and Bexxar®, irinotecan, leustatin, vinorelbine, STI-571 (Gleevac®), tamoxifen, docetaxel, topotecan, capecetabine (Xeloda®), raltitrexed, streptozocin, tegafur with uracil, temozolomide, thioguanine, thiotepa, podophyllotoxin, filgristim, profimer sodium, letrozole, amifostine, anastrozole, temozolomide, arsenic trioxide, epithalones A and B tretinioin, interleukins (e.g., 2 and 12) and interferons, e.g., alpha and gamma, bortezomib, huBr-E3, Genasense, Ganite, FIT-3 ligand, MLN491RL, MLN2704, MLN576, and MLN518. Antiangiogenic agents include but are not limited to BMS-275291, Dalteparin (Fragmin®) 2-methoxyestradiol (2-ME), thalodmide, CC-5013 (thalidomide analog), maspin, combretastatin A4 phosphate, LY317615, soy isoflavone (genistein; soy protein isolate), AE-941 (Neovastat™; GW786034), anti-VEGF antibody (Bevacizumab; Avastin™), PTK787/ZK 222584, VEGF-trap, ZD6474, EMD 121974, anti-anb3 integrin antibody (Medi-522; Vitaxin™), carboxyamidotriazole (CAI), celecoxib (Celebrex®), halofuginone hydrobromide (Tempostatin™), and Rofecoxib (VIOXX®).

The term "chemotherapy" also includes gene therapy with agents such as interferon and the interleukins, i.e., administration of a vector encoding genes for the interferons or interleukins. See e.g., Heller et al., Technol Cancer Res Treat. 2002; 1(3):205-9.

The term "PXR/SXR" refers to a mammalian steroid and xenobiotic-sensing nuclear receptor. For example, the nucleotide and amino acid sequences for the human PXR/SXR can be found in GenBank Accession No. AY091855, or in Blumberg et al., Genes Dev. 1988; 12(20: 3195-3205.

"Cell cycle regulatory proteins" are those proteins, including enzymes, which are required for progression through the cell cycle, i.e., mitosis, or arrest of the cell cycle, i.e., senescence. Cell cycle progression proteins include but are not limited to CDC25A, CDC2, Wee-1, Myt-1, cyclin A, cyclin B, and LATS1, and associated cyclin dependent kinases. Proteins involved in cell cycle arrest, which include DNA repair proteins, include but are not limited to Id-1, Id-2, Id-3, ATM, ATR, p53, BRCA-1, BRCA-2, chk-1, Rad-53, and the cyclin dependent kinase inhibitors.

As used herein, the terms "treatment" or "treat" mean the lessening or ameliorating of at least one abnormal or undesirable condition associated with cancer. Treatment may, for example, cause a reduction in the rate or amount of growth of a tumor. Treatment also includes reducing or ameliorating the undesirable symptoms of cancer. The foregoing are merely non-limiting examples of the treatment of cancer. In a specific embodiment, the term "treatment" refers to enhancing tumor cell death by RT and/or CT by administering PABA derivatives.

As used herein, a "therapeutically effective amount" of an agent is an amount sufficient to ameliorate at least one symptom associated with a pathological, abnormal or otherwise undesirable condition, e.g., cancer, an amount sufficient to prevent or lessen the probability that such a condition will occur or re-occur, or an amount sufficient to delay worsening of such a condition. In one embodiment, the term "therapeutically effective amount" is used to refer to an amount having antiproliferative effect.

Preferably, the therapeutically effective amount has apoptotic activity, or is capable of inducing cell death, and preferably death of benign or malignant tumor cells, in particular cancer cells. Efficacy can be measured in conventional ways, depending on the condition to be treated. For cancer therapy, efficacy can, for example, be measured by assessing the time for disease progression, or determining the response rates. In a preferred embodiment, and effective amount of PABA is an amount that reduces or inhibits the growth and/or proliferation of tumor cells in an individual in need of treatment alone, or in combination with RT or CT.

As used herein, the phrase "individual or mammal in need of such treatment" refers to a mammal suffering from at least one type of hyperproliferative disorder or who has been diagnosed with cancer.

The phrase "in combination with" refers to a method of treatment in which two or more treatments are administered collectively or according to a specific sequence, such that they produce a desirable effect.

The term "potentiate" means to increase the effect of, or act synergistically with, a drug or a biologic. In one embodiment of the present invention, PABA derivatives potentiate the tumorcidal activity or inhibition of tumor growth effected by RT or CT.

As used herein, the term "lead compound" or "candidate compound" is a compound that i) inhibits tyrosinase in melanoma cells, e.g., C-45, or ii) binds to and activates the PXR/SXR receptor. In a preferred embodiment, the lead compounds are benzoic acid derivatives, including but not limited to those depicted in FIG. 1.

The phrase "pharmaceutically acceptable" refers to molecular entities and compositions that are physiologically tolerable and do not typically produce an allergic or similar toxicity (for example, gastric upset, dizziness and the like) when administered to an individual. Preferably, and particularly where a formulation is used in humans, the term "pharmaceutically acceptable" may mean approved by a regulatory agency (for example, the U.S. Food and Drug Agency) or listed in a generally recognized pharmacopeia for use in animals (e.g., the U.S. Pharmacopeia).

The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

Molecular Biology

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, and other methods known in the art. In a specific embodiment, purified means that the level of contaminants is below a level acceptable to regulatory authorities for administration to a human or non-human animal.

A "gene" is a sequence of nucleotides which code for a functional "gene product". Generally, a gene product is a functional protein. However, a gene product can also be another type of molecule in a cell, such as an RNA (e.g., a tRNA or a rRNA). For the purposes of the present invention, a gene product also refers to an mRNA sequence which may be found in a cell.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (e.g., a mRNA or a rRNA) or a protein. The expression product itself, e.g., the resulting RNA or protein, may also said to be "expressed" by the cell.

"Expression level" correspond to levels of a detectable cellular product e.g., mRNA or a corresponding gene product, or an activity of such a gene product. For example, according to the screening method of present invention, changes in the expression level of a reporter gene operatively associated with the PXR/SXR response element can be used to determine whether a compound binds to and activates the PXR/SXR receptor.

The term "transfection" means the introduction of a foreign nucleic acid into a cell. The term "transformation" means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence.

The term "expression system" means a host cell and compatible vector under suitable conditions, e.g., for the expression of a protein coded for by foreign DNA carried by the vector and introduced to the host cell. Common expression systems include *E. coli* host cells and plasmid vectors, insect host cells such as Sf9, Hi5 or S2 cells and *Baculovirus* vectors, and expression systems, and mammalian host cells, including tumor cells and cell lines, and vectors.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

Screening

The ability to screen compounds for the capability to inhibit tyrosinase, or to bind and activate the PXR/SXR receptors, will permit the identification and selection of lead compounds for the improved treatment of melanoma and other cancers, or for the treatment of tumors which express PXR/SXR receptors when combined with standard treatment, e.g., CT or RT. For the latter, compounds that are preferred are those that differentially up-regulate cell cycle progression proteins such as CDC25A, and down-regulate DNA repair proteins such as BRCA-2.

Screening can be achieved by any method known in the art, including but not limited to the methods described below in the Examples, by using cell-free and cell-based, and high-throughput methods described further below.

In vitro Screening Methods

Various assays can be designed to screen for PABA-like inhibitors of tyrosinase, or agonists of PXR/SXR. Although in vitro methods are preferred for any initial screening of large number of potential drug candidates or agents, the in vivo methods described below may also be used for screening.

Tyrosinase inhibitors. The tyrosinase inhibitors may be both direct and indirect inhibitors. Preferred, although non-limiting, examples of indirect inhibitors include anti-sense nucleic acids complementary to genomic DNA or mRNA encoding tyrosinase, thus preventing translation of the coding nucleic acid sequences into the target protein. Methods to design and screen for antisense nucleic acids are well-known in the art. Thus, anti-sense sequences may be used to modulate the activity of the drug target or to achieve regulation of gene function. Sense or anti-sense oligomers, or larger fragments, can be designed from various locations along the coding or regulatory regions of sequences encoding a drug target of the invention.

Alternative indirect inhibitors include compounds, such as the exemplified benzoic acid derivative C-45, that reduce transcription of the gene encoding the target protein, i.e., tyrosinase.

Direct inhibitors of tyrosinase can be identified by evaluating the inhibitory effect of a drug candidate or test agent on the biological activity of the selected target protein ("drug target") in comparison to a control or reference. The control or reference may be a predetermined reference value, or may be evaluated experimentally. For example, the control or reference value can be a measure of the biological activity of the target protein in the absence of the test agent, or the biological activity of a reference protein in the presence of test agent, or any other suitable control or reference.

Drugs or agents that inhibit the activity of a target protein, e.g., tyrosinase, can be identified based on their ability to associate with the drug target protein. Association with a drug target can be tested by reacting a drug target protein or fragment with a test substance which has the potential to associate with the drug target under appropriate conditions, and removing and/or detecting the associated drug target/test substance complex. Binding may be detected by indirect or direct functional measures such as alteration of migration pattern in protein gel electrophoresis, immunoprecipitation, or the Biomolecular Interaction Assay (BIAcore; Pharmacia). A drug candidate that associates with a drug target protein of the invention is preferably an antagonist or inhibitor of the biological activity of a drug target, as shown by an activity assay.

Activity assays are generally designed to measure the activity of a target protein in the presence or absence of a test agent. Many different activity assays may be designed based on various art-recognized methods for studying the activity of tyrosinase. For example, as described in Example 1, inhibitors of tyrosinase activity can be identified by measuring the ability of tyrosinase to promote the conversion of a L-DOPA into a DOPAochrome over a suitable period of time, as detected by measuring absorbance. Optionally, in cases where the substrate is detectable by fluorescence or by coloring, the amount of intact substrate remaining can be measured after incubation for suitable time period.

PXR/SXR agonists. To assess PXR/SXR binding and activation by test compounds and other benzoic acid derivatives, standard cell-based reporter assays can be employed. This technique involves transfecting target cells with a reporter construct carrying the xenobiotic response elements (e.g., DR3 motif 5' AGTTCA 3') upstream of e.g., a luciferase reporter gene. Following treatment of cells with e.g., PABA or any other test compound, activation of the PXR/SXR-receptors will be quantified by measuring the increase in luciferase activity as a result of activation of the receptors and their binding to the xenobiotic response elements (Kliewer et al., Cell 1998; 92: 73-82; and Takeshita et al., J. Biol. Chem. 2002; 277: 32453-8).

In addition, screening for compounds affecting PXR/SXR binding or activity in the presence of test substances, additional reporter gene assays which be used include a green fluorescent protein expression system, and modifications thereof (U.S. Pat. No. 5,625,048 and PCT Publication No. WO 98/06737; PCT Publication No. WO 96/23898). Other reporter genes include β-galactosidase (β-gal or lac-Z), chloramphenicol transferase (CAT), horseradish peroxidase, and alkaline phosphatase.

In addition, levels of CDC25A and BRCA-2 and other cell cycle-related proteins, such as Id-1, Id-2 and Id-3, in response to drug treatment can be determined using specific antibodies, e.g., by standard immunoblotting or other quantification assays well known in the art.

Nucleic acid expression, such as mRNA expression, can be determined by standard RT-PCR and/or Northern hybridization techniques.

In addition to screening, the role of the PXR/SXR receptor in PABA induced radio- and chemosensitization can be further elucidated by silencing the PXR/SXR receptor, e.g., using siRNA technology, and assessing the effect of PABA and related derivative compounds on cell cycle-associated proteins such as CDC25A, Id-1, Id-2, Id-3 and BRCA-2.

Compound Libraries

In addition to the PABA-derivatives described herein as PXR/SXR agonists, synthetic libraries provide a source of potential agonists according to the present invention libraries (Needels et al., Proc. Natl. Acad. Sci. USA 1993, 90:10700-4; Ohlmeyer et al., Proc. Natl. Acad. Sci. USA 1993, 90:10922-10926; Lam et al., PCT Publication No. WO 92/00252; Kocis et al., PCT Publication No. WO 9428028). Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available, e.g., from Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech 1996, 14:60).

Another approach uses recombinant bacteriophages to produce large libraries. Using the "phage method", very large libraries can be constructed (106-108 chemical entities) (Scott and Smith, Science 1990, 249:386-390; Cwirla, et al., Proc. Natl. Acad. Sci. USA 1990, 87:6378-6382; Devlin et al., Science 1990, 49:404-406). A alternative approach uses primarily chemical methods, of which the Geysen method (Geysen et al., Molecular Immunology 1986, 23:709-715; Geysen et al. J. Immunologic Methods 1987, 102:259-274); and the method of Fodor et al. (Science 1991, 251:767-773) are examples.

Classes of compounds that may be identified by such screening assays include, but are not limited to, small molecules (e.g., organic or inorganic molecules which are less than about 2 kd in molecular weight, are more preferably less than about 1 kD in molecular weight, and/or are able to cross the blood-brain barrier or gain entry into an appropriate cell, as well as macromolecules (e.g., molecules greater than about 2 kD in molecular weight).

The compounds used in such screening assays are also preferably essential pure and free of contaminants that may, themselves, alter or influence gene expression. Compound purity may be assessed by any number of means that are routine in the art, such as LC-MS and NMR spectroscopy. Libraries of test compounds are also preferably biased by using computational selection methods that are routine in the art. Tools for such computational selection, such as Pipeline Pilot™ (Scitegic Inc., San Diego, Calif.) are commercially available. The compounds may be assessed using rules such as the "Lipinski criteria" (see, Lipinski et al., Adv. Drug Deliv. Rev. 2001, 46:3-26) and/or an other criteria or metrics commonly used in the arts.

High-Throughput Screening

The in vitro assay systems described here may be used in a high-throughput primary screen for compounds. For example, drug candidates according to the invention may advantageously be identified by screening in high-throughput assays, including without limitation cell-based or cell-free assays. It will be appreciated by those skilled in the art that different types of assays can be used to detect different types of drugs or agents. Several methods of automated assays have been developed in recent years so as to permit screening of tens of thousands of compounds in a short period of time (see, e.g., U.S. Pat. Nos. 6,303,322, 5,585,277, 5,679,582, and 6,020,141). Such high-throughput screening methods are particularly preferred. Identifying agents is greatly facilitated by use of high-throughput screening assays to test for agents together with large amounts of drug candidates, provided as described herein.

In vivo Screening Methods

The in vivo chick embryo and mouse xenograft models of the invention can advantageously be used for testing the efficacy of a drug identified as a candidate drug in an in vitro screen, and for optimizing dosages and administration schedules of the drug candidate to enhance anti-proliferative effects of CT and RT. In one embodiment of the invention, drugs that inhibit the activity of tyrosinase or agonize activity of the PXR/SXR receptor, and are therefore candidates for potentiating the tumoricidal effects of CT and RT, are evaluated as described in Examples 1-6 below.

Formulations and Administration

Formulations

For use in the present invention, PABA may be formulated into a pharmaceutical composition. The pharmaceutical composition may include additives, such as a pharmaceutically acceptable carrier or diluent, a flavorant, a sweetener, a preservative, a dye, a binder, a suspending agent, a dispersing agent, a colorant, a disintegrant, an excipient, a film forming agent, a lubricant, a plasticizer, an edible oil or any combination of two or more of the foregoing.

Suitable pharmaceutically acceptable carriers or diluents include, but are not limited to, ethanol, water, glycerol, propylene glycol, aloe vera gel, allantoin, glycerin, vitamin A and E oils, mineral oil, PPG2 myristyl propionate, magnesium carbonate, potassium phosphate, vegetable oil, animal oil, and solketal. Preferred carriers are vegetable and mineral oils.

Suitable binders include, but are not limited to, starch, gelatin, natural sugars, such as glucose, sucrose and lactose; corn sweeteners, natural and synthetic gums, such as acacia, tragacanth, vegetable gum, and sodium alginate, carboxymethylcellulose, hydroxypropylmethylcellulose, polyethylene glycol, povidone, waxes; and the like.

Suitable disintegrants include, but are not limited to, starch, e.g., corn starch, methyl cellulose, agar, bentonite, xanthan gum, sodium starch glycolate, crosspovidone and the like.

Suitable lubricants include, but are not limited to, sodium oleate, sodium stearate, sodium stearyl fumarate, magnesium stearate, sodium benzoate, sodium acetate, sodium chloride and the like.

A suitable suspending agent is, but is not limited to, bentonite, ethoxylated isostearyl alcohols, polyoxyethylene sorbitol and sorbitan esters, microcrystalline cellulose, aluminum metahydroxide, agar-agar and tragacanth, or mixtures of two or more of these substances, and the like.

Suitable dispersing and suspending agents include, but are not limited to, synthetic and natural gums, such as vegetable gum, tragacanth, acacia, alginate, dextran, sodium carboxymethylcellulose, methylcellulose, polyvinyl-pyrrolidone and gelatin.

Suitable film forming agents include, but are not limited to, hydroxypropylmethylcellulose, ethylcellulose and polymethacrylates.

Suitable plasticizers include, but are not limited to, polyethylene glycols of different molecular weights (e.g., 200-8000 Da) and propylene glycol.

Suitable colorants include, but are not limited to, ferric oxide(s), titanium dioxide and natural and synthetic lakes.

Suitable edible oils include, but are not limited to, cottonseed oil, sesame oil, coconut oil and peanut oil.

Examples of additional additives include, but are not limited to, sorbitol, talc, stearic acid, dicalcium phosphate and polydextrose.

Dosages and Dosage Forms

The pharmaceutical composition or unit dosage form of the present invention, i.e., a benzoic acid derivative such as C-45, may be administered according to a dosage and administration regimen defined by routine testing in order to obtain optimal activity while minimizing toxicity or side-effects for a particular patient. Typically, dosages will determined by those skilled in the art on a case-by-case basis, depending upon the tumor type, stage, location, and prognosis of the individual, and other factors such as weight, sex and age of the individual, the particular dosage form employed, and the route of administration utilized. Pharmacokinetics and pharmacodynamics such as half-life ($t_{1/2}$), peak plasma concentration ($c_{max}$), time to peak plasma concentration ($t_{max}$), and exposure as measured by area under the curve (AUC) can be obtained using ordinary methods known in the art.

Data obtained from cell culture assay or animal studies may be used to formulate a therapeutic dosage range for use in humans and non-human animals. The dosage of compounds used in therapeutic methods of the present invention preferably lie within a range of circulating concentrations that includes the $ED_{50}$ concentration (effective for 50% of the tested population) but with little or no toxicity.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms (e.g., as determined from the cell culture assays). Appropriate dosages for use in a particular individual, for example in human patients, may then be more accurately determined using such information.

In one embodiment, the compound may be administered, alone or in combination with CT or RT in the range of about 10 g/day, preferably in a range from about 10 mg/day to about 6 g/day, more preferably in a range from about 250 mg/day to about 5 g/day.

For combination therapy with radiation, the radiation is typically administered in doses of 1 cGy to 100 Gy. More preferably, radiation is administered in doses of 2 cGy to 20 Gy. Factors such as dose rate delivered, tumor size, and radiosensitivity play a major role in determining therapeutic response, while target-to-nontarget ratios and, particularly, circulating radioactivity to the bone marrow determine the major dose-limiting toxicities.

Dosages of chemotherapy are not only drug-type specific, but also depend to a large extent on the individual patient, the tumor-type, and the stage of the disease, and accordingly, are determined by one of ordinary skill in the art. By way of example, standard doses of paclitaxel (TAXOL®) in combination with carboplatin for ovarian and lung cancer are 175 $mg/m^2$ of the former and AUC 5 mg/ml*min of the latter.

Unit dosage forms. The above compositions of the benzoic acid derivatives may be formulated as unit dosage forms such as tablets, pills, capsules, caplets, boluses, powders, granules, sterile parenteral solutions, sterile parenteral suspensions, sterile parenteral emulsions, elixirs, tinctures, metered aerosol or liquid sprays, drops, ampoules, autoinjector devices or suppositories. Unit dosage forms may be used for oral, parenteral, intranasal, sublingual or rectal administration, or for administration by inhalation or insufflation, transdermal patches, and a lyophilized composition. In general, any delivery of active ingredients that results in systemic availability of them can be used.

Preferably the unit dosage form of the benzoic acid derivative is an oral dosage form, most preferably a solid oral dosage form, therefore the preferred dosage forms are tablets, pills, caplets and capsules. PABA-derivative-containing solutions and suspensions for oral administration are also preferred. However, the compound can also be formulated for parenteral administration. Parenteral preparations (e.g., injectable preparations in saline and preparations for powder jet systems) are preferred for CT and RIT.

Solid unit dosage forms may be prepared by mixing an active agent of the present invention with a pharmaceutically acceptable carrier and any other desired additives as described above. The mixture is typically mixed until a homogeneous mixture of the active agents of the present invention and the carrier and any other desired additives is formed, i.e., until the active agent is dispersed evenly throughout the composition. In this case, the compositions can be formed as dry or moist granules.

Dosage forms with predetermined amounts of the benzoic acid derivatives may be formulated starting with compositions with known quantities of the compounds using methods well known in the art. In a preferred embodiment a dosage form is obtained by mixing compositions comprising known quantities of the derivatives.

Dosage forms can be formulated as, for example, "immediate release" dosage forms. "Immediate release" dosage forms are typically formulated as tablets that release at least 70%-90% of the active ingredient within 30-60 min when tested in a drug dissolution test, e.g., U.S. Pharmacopeia standard <711>. In a preferred embodiment, immediate dosage forms release 75% of active ingredients in 45 min.

Dosage forms can also be formulated as, for example, "controlled release" dosage forms. "Controlled," "sustained," "extended" or "time release" dosage forms are equivalent terms that describe the type of active agent delivery that occurs when the active agent is released from a delivery vehicle at an ascertainable and modifiable rate over a period of time, which is generally on the order of minutes, hours or days, typically ranging from about sixty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract. Typical parameters for dissolution test of controlled release forms are found in U.S. Pharmacopeia standard chapter <724>.

Dosage forms can also be formulated to deliver active agent in multiphasic stages whereby a first fraction of an active ingredient is released at a first rate and at least a second fraction of active ingredient is released at a second rate. In a preferred embodiment, a dosage form can be formulated to deliver active agent in a biphasic manner, comprising a first "immediate release phase", wherein a fraction of active ingredient is delivered at a rate set forth above for immediate release dosage forms, and a second "controlled release phase," wherein the remainder of the active ingredient is released in a controlled release manner, as set forth above for controlled release dosage forms.

Tablets or pills can be coated or otherwise compounded to form a unit dosage form which has delayed and/or prolonged action, such as time release and controlled release unit dosage forms. For example, the tablet or pill can comprise an inner dosage and an outer dosage component, the latter being in the form of a layer or envelope over the former. The two components can be separated by an enteric layer which serves to resist disintegration in the stomach and permits the inner component to pass intact into the duodenum or to be delayed in release.

Biodegradable polymers for controlling the release of the active agents, include, but are not limited to, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For liquid dosage forms, the active substances or their physiologically acceptable salts are brought into solution, suspension or emulsion, optionally with the usually employed substances such as solubilizers, emulsifiers or other auxiliaries. Solvents for the active combinations and the corresponding physiologically acceptable salts, can include water, physiological salt solutions or alcohols, e.g. ethanol, propane-diol or glycerol. Additionally, sugar solutions such as glucose or mannitol solutions may be used. A mixture of the various solvents mentioned may further be used in the present invention.

A transdermal dosage form also is contemplated by the present invention. Transdermal forms may be a diffusion-driven transdermal system (transdermal patch) using either a fluid reservoir or a drug-in-adhesive matrix system. Other transdermal dosage forms include, but are not limited to, topical gels, lotions, ointments, transmucosal systems and devices, and iontohoretic (electrical diffusion) delivery system. Transdermal dosage forms may be used for timed release and controlled release of the active agents of the present invention.

Pharmaceutical compositions and unit dosage forms of the present invention for administration parenterally, and in particular by injection, typically include a pharmaceutically acceptable carrier, as described above. A preferred liquid carrier is vegetable oil. Injection may be, for example, intravenous, intrathecal, intramuscular, intratracheal, or subcutaneous.

The active agent also can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The benzoic acid derivatives of the present invention also may be coupled with soluble polymers as targetable drug carriers. Such polymers include, but are not limited to, polyvinyl-pyrrolidone, pyran copolymer, polyhydroxypropyl-methacryl-amidephenol, polyhydroxy-ethylaspartamidephenol, and polyethyl-eneoxideopolylysine substituted with palmitoyl residues.

Administration

The pharmaceutical composition or unit dosage forms of the present invention may be administered by a variety of routes such as intravenous, intratracheal, subcutaneous, oral, intratumoral, mucosal parenteral, buccal, sublingual, rectal, ophthalmic, pulmonary, transmucosal, transdermal, and intramuscular. Unit dosage forms also can be administered in intranasal form via topical use of suitable intranasal vehicles, or via transdermal routes, using those forms of transdermal skin patches known to those of ordinary skill in the art. Oral administration of the derivatives is preferred. Also preferred is administration by local intratumoral injection.

The pharmaceutical composition or unit dosage forms of the present invention may be administered to a mammal, preferably a human being, in need of cancer treatment.

The pharmaceutical composition or unit dosage form may be administered in a single daily dose, or the total daily dosage may be administered in divided doses. In addition, co-administration or sequential administration of other active agents may be desirable. The derivatives and mixtures thereof of the invention may be combined with any known drug therapy, preferably RT and/or CT, for the treatment of cancer.

The pharmaceutical composition or unit dosage form may be administered in a single daily dose, or the total daily dosage may be administered in divided doses. The combination of the benzoic acid derivative and RT or CT may be co-administered simultaneously or sequentially administered. The compounds preferably will be provided as separate dosage forms.

The exact dosage and administration regimen utilizing the combination therapy of the present invention is selected in accordance with a variety of factors including type, species, age, weight, sex and medical condition of the patient; the route of administration; the renal and hepatic function of the patient; the treatment history of the patient; and the responsiveness of the patient. Optimal precision in achieving concentrations of compounds within the range that yields efficacy without toxicity requires a regimen based on the kinetics of the drug's availability to target sites. This involves a consideration of the absorption, distribution, metabolism, excretion of a drug, and responsiveness of the patient to the dosage regimen. However, such fine tuning of the therapeutic regimen is routine in light of the guidelines given herein.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

PABA and Derivatives Inhibit Tyrosinase Activity in vitro

Methods

Activity of purified tyrosinase was measured by monitoring the formation of DOPAchrome. Briefly, a fixed concentration of L-DOPA (8.0 mM) was incubated with 800 U/ml tyrosinase (from mushrooms-Sigma, St. Louis, Mo.) in the absence or presence of increasing concentrations of PABA, compound 44 (C-44) and compound 45 (C-45) (see FIG. 1 for structures) for indicated time points (see FIG. 2 for concentrations and time points). At each time point, 100 µl of the reaction mixture was measured. Data points represent the mean optical density at 475 nm±SD from triplicate wells.

Results

Figure 2:
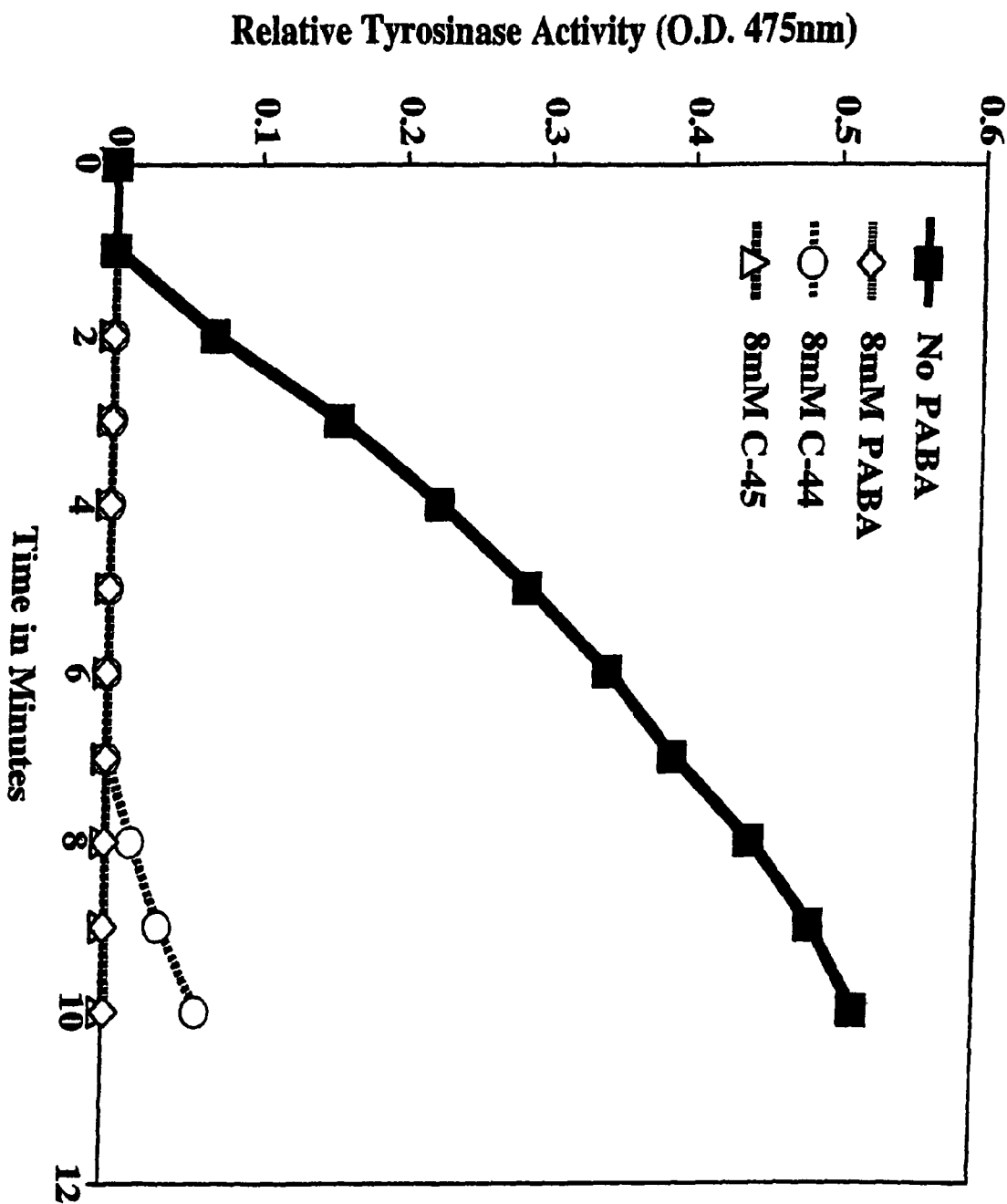
FIG. 2 demonstrates the inhibition of tyrosinase over time with PABA and two derivative compounds.

As shown in FIG. 2, PABA, C-44, and C-45 all inhibited tyrosinase activity at 8.0 mM up to 10 minutes, the last time point measured. By contrast, untreated samples demonstrated linearly increasing tyrosinase activity up to 10 minutes. This approach can be applied to evaluate other benzoic acid derivatives or other compounds for inhibitory activity on tyrosinase.

Example 2

Effects of PABA Derivative C-45 on Carcinoma Cells Treated with Chemotherapy

Methods

Tumor cell proliferation was assessed by monitoring mitochondrial dehydrogenase activity as detected by tetrazolium salt cleavage using a commercially available kit (WST-1; Roch, Indianapolis, Ind.). Briefly, B16F10 melanoma cells, Lewis Lung carcinoma cells, and 4T1 breast carcinoma cells ($1\times10^6$) were resuspended in PABA-free growth medium supplemented with 2.0% fetal bovine serum and 50 µg/ml of test compound (as shown in FIG. 1). Following incubation for 3 days, the cells were either treated or not treated with 0.01 µM TAXOL® (paclitaxel) and incubated for an additional 48 hours. Proliferation was measured; data points represent the mean optical density at 490 nm±SD from, triplicate wells.

In addition, tumor growth in vivo of xenografts of B16F10 melanoma cells in nude mice was determined. Briefly, subconfluent cultures of B16F10 cells were harvested, washed, and resuspended in sterile PBS. Female nude mice were injected subcutaneously with $1\times10^6$ cells per mouse and tumors were allowed to grow for 3 days. After 3 days, mice were either untreated or treated daily for 15 days by intraperitoneal injection of TAXOL® (paclitaxel) (0.5 µM), C-45 (100 µg), or a combination of TAXOL® (paclitaxel) and C-45. Tumor growth was determined weekly by caliper measurements. After 15 days, the mice were sacrificed and tumor volume was determined by standard methods using the formula V=L×W/2, where V=volume, L=length, and W=width.

Results

Figure 3A:
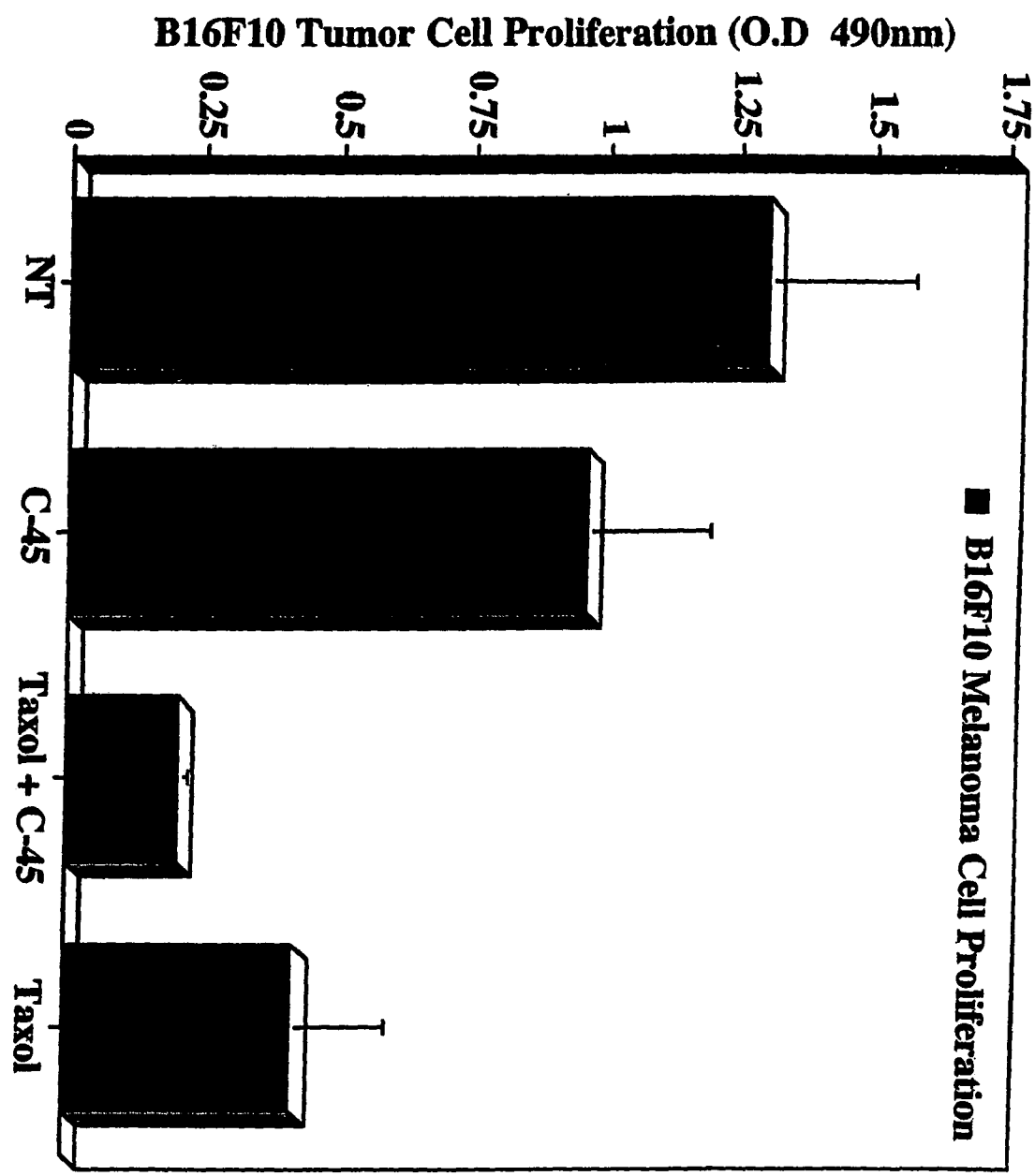
FIG. 3 shows in vivo effects on the proliferation of B16F10 (3A), Lewis Lung carcinoma (3B), and 4T1 (3C) breast carcinoma cells treated with compound C-45, TAXOL® (paclitaxel), and a combination of C-45 and TAXOL® (paclitaxel).
Figure 3B:
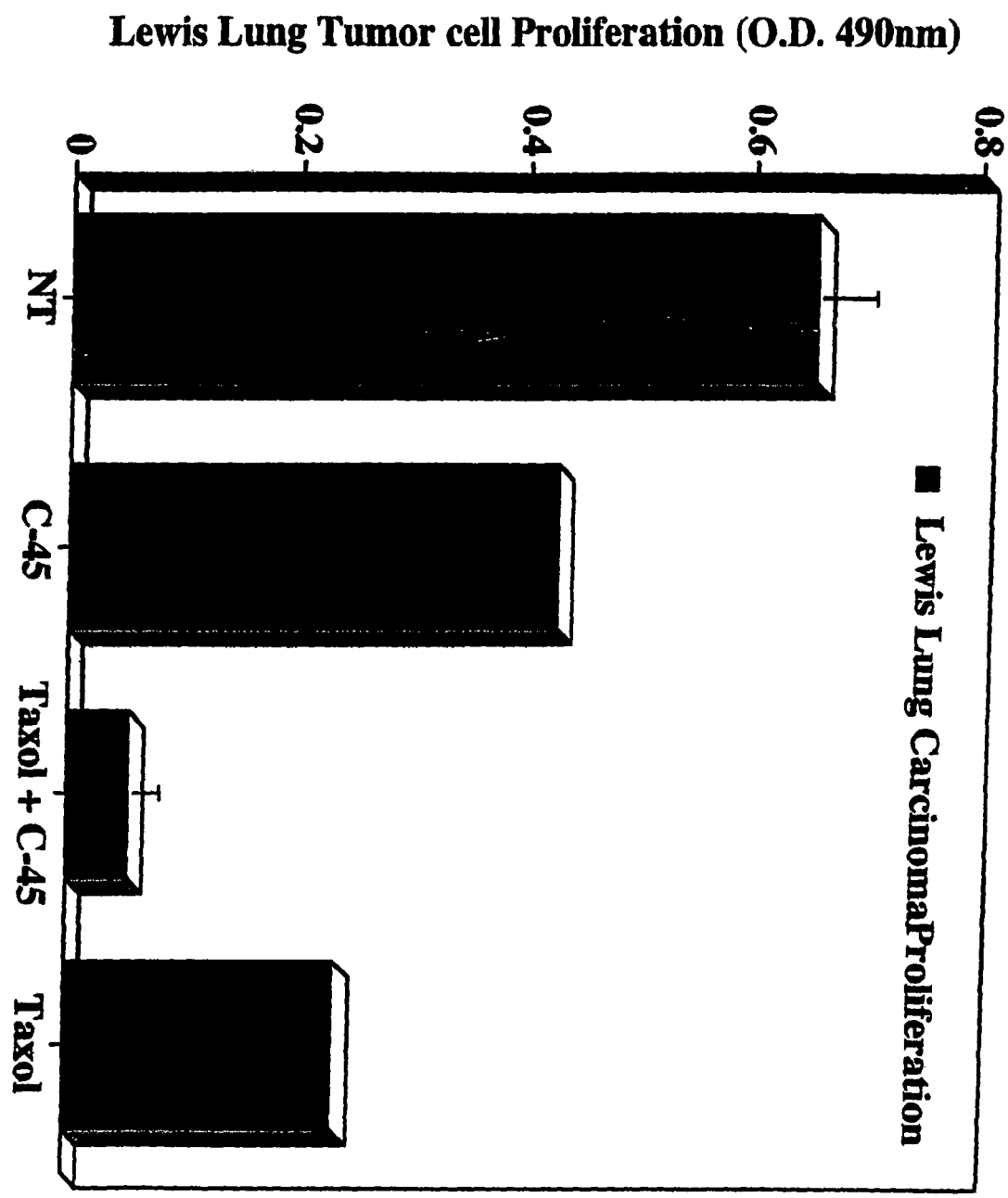
Figure 3C:
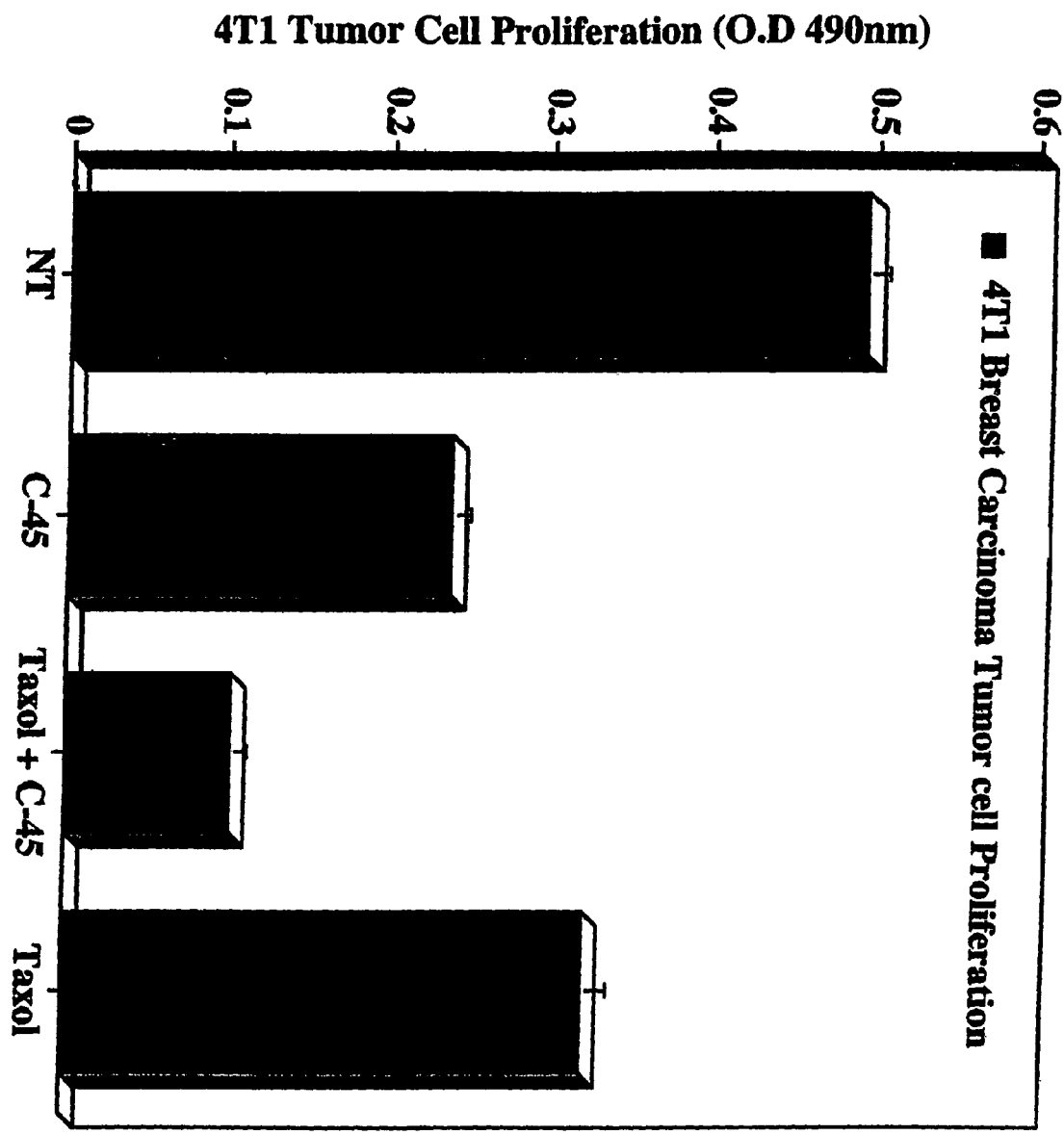

FIGS. 3A-C demonstrate that both TAXOL® (paclitaxel) and compound C-45 individually inhibited in vitro proliferation of B16F10, Lewis Lung carcinoma, and 4T1 breast carcinoma cells compared to untreated control, and the inhibition was even more pronounced with a combination of C-45 and TAXOL® (paclitaxel).

Figure 4:
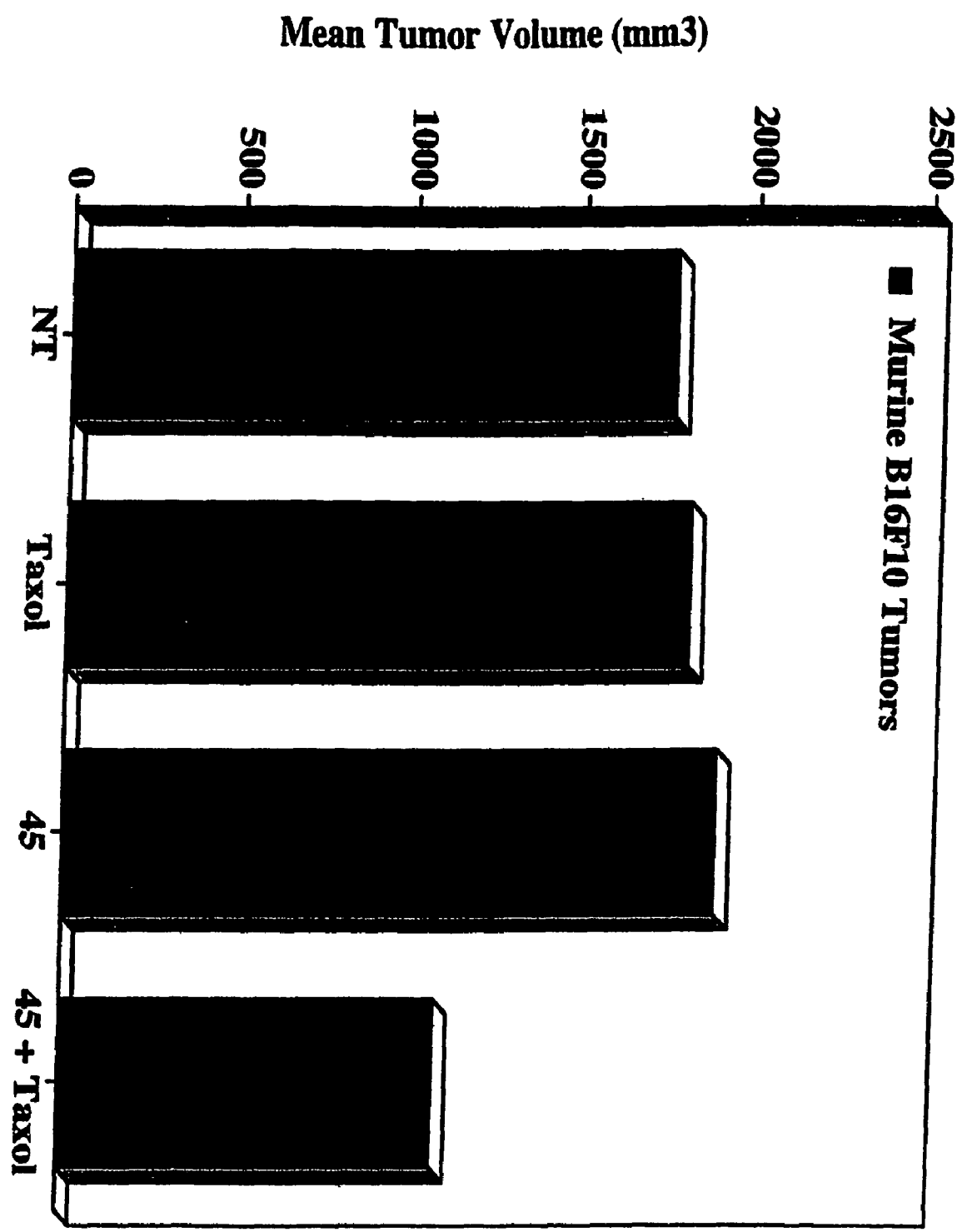
FIG. 4 shows the in vivo effects of compound C-45, TAXOL® (paclitaxel), and a combination thereof, on tumor growth in nude mice.

As shown in FIG. 4, neither TAXOL® (paclitaxel) nor C-45 inhibited in vivo tumor growth compared to untreated controls. By contrast, a combination of TAXOL® (paclitaxel) and C-45 inhibited in vivo growth by more than about 33%.

Example 3

The Effect of C-45 on Radio- and Chemosensitivity in vivo

Methods

The chick embryo tumor growth model was used to determine whether C-45 enhances the ability of TAXOL® (paclitaxel) or ionizing radiation to inhibit tumor growth. Briefly B16F10 melanoma cells were cultured in growth medium in the presence or absence of 50 µg/ml C-45 for at least 7 days. Following harvesting and washing, about $2\times10^5$ tumor cells were implanted onto the chorioallontoic membranes of 10 day-old chick embryos and incubated for at least 24 hours. Following incubation, the embryos were treated with either a single fractionated dose of radiation (5.0 Gy) or TAXOL® (paclitaxel) (0.01 µM) and incubated for an additional 7 days. The embryos were sacrificed and tumors were resected and weighed (5-10 embryos per condition).

Results

Figure 5A:
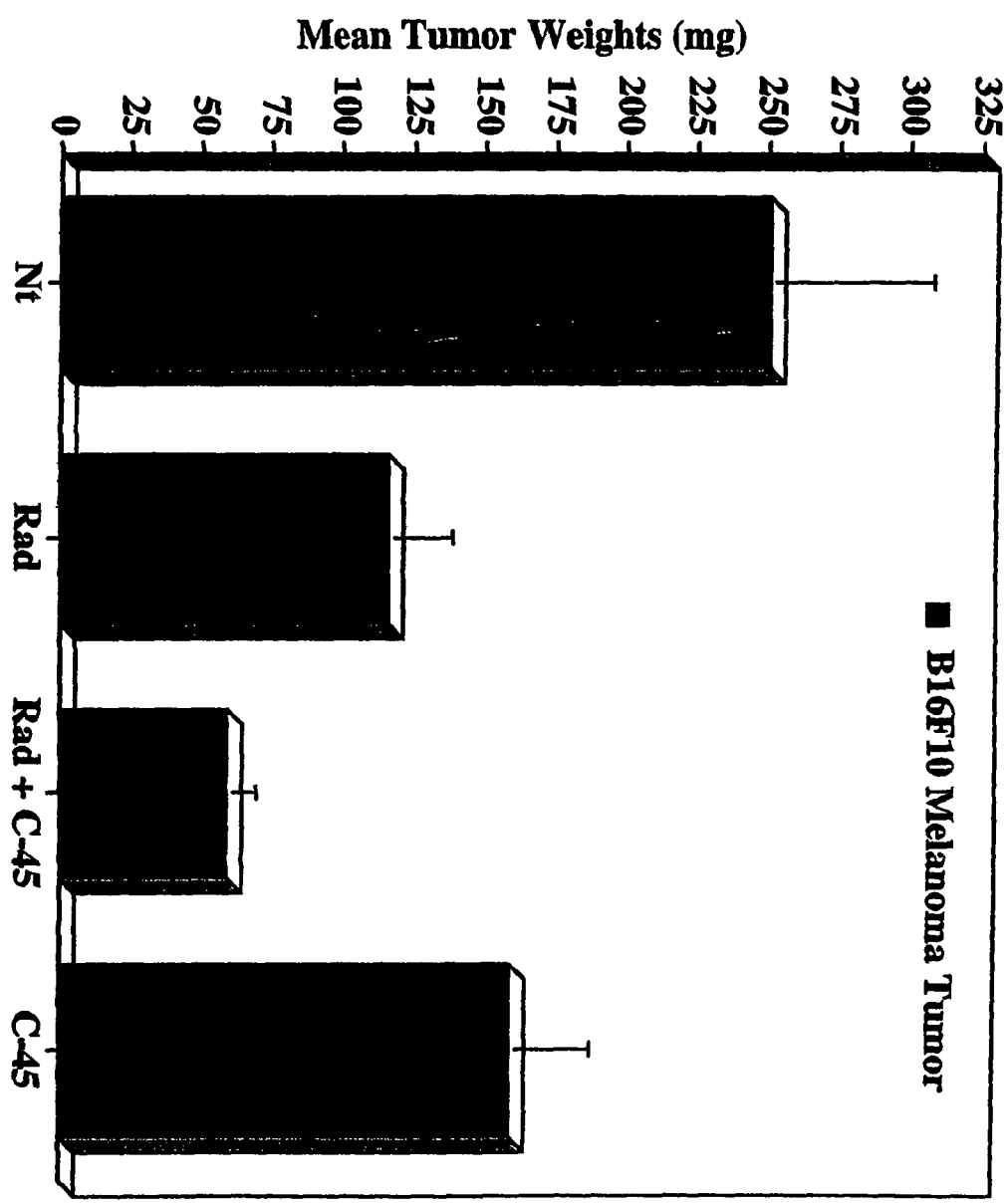
FIG. 5 demonstrates the effects of C-45, alone, and in combination with radiation- (5A) and chemotherapy (5B), on growth of the B16F10 melanoma tumors in chick embryos.
Figure 5B:
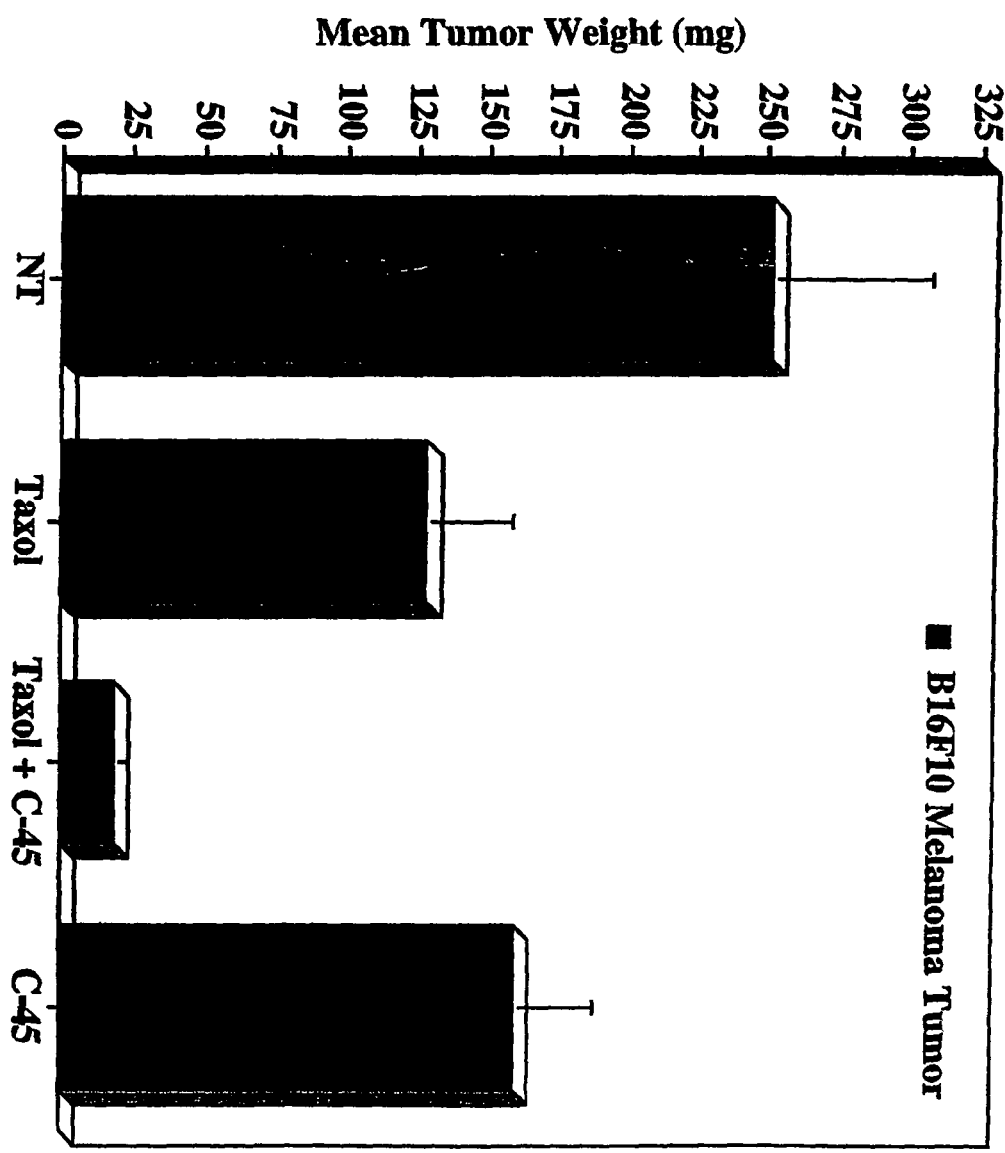

FIG. 5A-B demonstrates the effect of C-45 on radiation- and chemotherapy-treated tumor growth in chick embryos. As shown in FIG. 5A, while treatment with radiation and C-45 alone reduced tumor weight significantly, the combination of radiation and C-45 was even more effective at inhibiting tumor growth in vivo. Similarly, while TAXOL® (paclitaxel) and C-45 individually inhibited the growth of B16F10 tumors significantly, the combination was far more effective (FIG. 5B).

Example 4

Screening for Compounds that Bind to and Activate the PXR/SXR Receptor

Rationale

It has been previously demonstrated that PABA and other benzoic acid derivatives bind to the PXR/SXR receptor (Moore et al., Mol. Endocrinol. 2002; 16: 977-86). The present inventors have shown that when treated with PABA, G361 human melanoma cells exhibit decreased protein expression of DNA repair protein BRCA-2 and increase expression of cell-cycle progression checkpoint protein CDC25A (data not shown). G361 melanoma cells also express the PXR/SXR receptor whereas non-transformed melanocytes do not (data not shown). Accordingly, it is expected that PABA-like benzoic acid derivatives may have similar agonist activity at this receptor may be useful in the treatment of PXR/SXR over-expressing tumors.

Methods

To assess PXR/SXR binding and activation by test compounds and other benzoic acid derivatives, standard cell-based reporter assays can be employed. For example, target cells can be transfected with a reporter construct carrying the xenobiotic response elements (e.g., DR3 motif 5' AGTTCA 3') upstream of e.g., a luciferase reporter gene. Following treatment of cells with e.g., PABA or any other test compound, activation of the PXR/SXR receptors will be quantified by measuring the increase in luciferase activity as a result of activation of the receptors and their binding to the xenobiotic response elements (Kliewer et al., Cell 1998; 92: 73-82; and Takeshita et al., J. Biol. Chem. 2002; 277: 32453-8).

Example 5

Determining Expression of PXR/SXR and Cell Cycle Regulatory Proteins in Tumor Cells in Response to Drug Treatment Methods To determine whether tumor cells abnormally express and signal through the PXR/SXR receptor compared to their non-transformed counterparts, and thus, candidates for treatment with PXR/SXR agonists, immortalized, non-transformed cells and sub-confluent transformed, tumorigenic cells will be cultured in the presence or absence of various concentrations of a known PXR/SXR activator, e.g., benzoic acid derivatives, and a negative control, e.g., streptomycin, for a pre-determined time e.g., 5 days. Cell lyses will be achieved as described above. Following lyses, about 15 µg/lane of protein will be loaded and separated by 10% SDS-PAGE, followed by transfer to nitrocellulose membranes. Membranes will then incubated in the presence of e.g., monoclonal antibody 39048, specific for the PXR/SXR nuclear receptor, followed by washing and labeling with a peroxidase-labeled secondary antibody.

Similarly, to evaluate expression of cell cycle proteins that may be regulated by PXR/SXR activation in response to drug treatment, membranes as prepared above will be incubated with commercially available monoclonal antibodies such as PC410 (Chemicon, Temecula, Calif.), directed against β-integrin, as a positive control, monoclonal antibody 3303, specific for BRCA-2 (QED Biosciences, San Diego, Calif.), and with monoclonal antibody AB-3, directed against CDC25A (NeoMakers Inc). Additional antibodies may include anti-Id-1 monoclonal antibody B30-1, anti-Id-2 monoclonal antibody B31-1 (BD PharMingen, San Jose, Calif.) and Id-3 monoclonal antibody 56209 (QED Biosciences, San Diego, Calif.). Peroxidase-labeled goat anti-mouse secondary antibodies will then be incubated after washing. Additional controls consisted of membranes probed with only either the primary or secondary antibodies.

Detection will be performed using laser scanning densitometry using a Nuclear Vision 760 system to compare relative expression levels of the proteins.

Results

As stated above, it has been previously demonstrated that G361 melanomas, but not immortalized but untransformed melanocytes, express high levels of PXR/SXR (data not shown), and increased levels of CDC25A and decreased levels of DNA repair protein BRCA-2 when treated with PXR/SXR agonist PABA. This suggests that therapeutic agents like PABA or related derivatives which are agonists for this receptor will be useful in the treatment of PXR/SXR over-expressing tumors.

This finding led to the hypothesis that that PABA derivatives may also enhance the effects of chemotherapy and ionizing radiation in a manner similar to previously shown by PABA, by preventing tumor cells senescence upon treatment. A compound that simultaneously inhibits cell cycle repair proteins and increasing the concentration of proteins that induce cell cycle progression will be a preferred drug candidate. Accordingly, it is expected that similar effects on DNA repair and cell cycle regulatory protein expression will be observed with other PXR/SXR agonists depicted in FIG. 1 or identified by the screening methods of the present invention.

Example 6

Effects of Candidate Compounds on the Cell Cycle and Anti-Proliferative Effects of Ionizing Radiation or Chemotherapy in vitro Methods To test the hypothesis stated above for benzoic acid derivatives that bind to the PXR/SXR receptor, cell cycle analysis can be performed as follows using Fluorescent Activated Cell Sorting (FACS) in cells treated with drug candidates and CT or RT. Immortalized cells and PXR/SXR-expressing transformed tumorigenic cells will be cultured in the presence or absence of various concentrations of a test compound, and positive and negative control compounds (e.g., PABA and streptomycin) for a designated time period. Next, cells will be synchronized by serum starvation for at least 24 hours, then cultured in serum-containing medium and treated with a test compound and control compounds, with or without various single fraction doses of radiation (e.g., 1, 2, 5, 10 and 20 Gy) or chemotherapy. At various time points (e.g., 1, 3, 6, 12 and 24 h) following serum stimulation, cells will be removed and washed with PBS and fixed for 1 hr with 70% ethanol at 4° C. Cells will then be washed several times with PBS and resuspended in RNAse staining buffer, commercially available from BD PharMingen, for 30 minutes on ice. Cell cycle analysis will be determined using a FACs Scan flow cytometer (Becton-Dickenson, San Jose, Calif.), and data collected using e.g., a Hewlett Packard HP9000 equipped with FAC-Scan software and analyzed using PC-Lysis software (also from Becton-Dickenson). At least 10,000 events will be collected with identical gating parameters on single cell populations and percentages of cells within G0/G1, S, G2 and M determined along with the apoptotic population.

In addition to cell cycle analysis, cell proliferation can be measured using methods such as e.g., tetrazzolium salt cleavage or incorporation of tritiated thymidine. For example, cells can be treated with test and control compounds, plated and incubated for 2 hours to permit cell adhesion. Plates will then be treated or not with various concentrations of ionizing radiation, e.g., 1, 2, 10 and 20 Gy, or chemotherapy e.g., 0-0.2 µM TAXOL® (paclitaxel). Proliferation of the cells will then be measured using, e.g., the WST-1 kit (tetrazolium salt cleavage). Data points representing the mean optical density at 490 nm from triplicate wells±SD will be obtained.

Results

It is expected that treatment of non-transformed cells, or cells not expressing the PXR/SXR receptor, will not have altered proliferation when contacted with test compounds, radiation or chemotherapy, or a combination of the test compound with either agent. To the contrary, tumor cells which express PXR/SXR will respond to agonist compounds, as demonstrated by increased cell death, which will be more pronounced in combination with radiation or chemotherapy. Such compounds will be designated candidate or lead compounds.

CONCLUSION

The results presented herein are the first demonstration that benzoic acid derivatives can potentiate radio- and chemosensitivity of tumor cells which overexpress the PXR/SXR nuclear receptor. Given the potential of PABA to induce radiosensitivity via a PXR/SXR dependent mechanism, taken together with the relatively limited expression of PXR/SXR receptor in normal cell types, it is likely that specific agonists will provide a novel, effective approach to enhance the antitumor activity of RT and CT in malignant cells but not normal cells.

In addition, the present invention discloses the surprising discovery that benzoic acid derivatives that inhibit tyrosinase, and hence, melanogenesis, can potentiate RT and CT activities in melanotic as well as non-melanin expressing carcinoma cells.

REFERENCES CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed:

1. A method for treating melanoma in a mammal, wherein said method comprises administering, to a mammal in need of treatment, a compound having the structure:

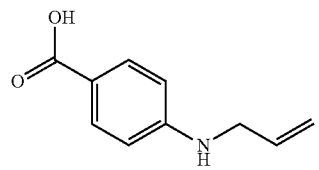

or a pharmaceutically acceptable salt thereof, and wherein the compound is administered in combination with paclitaxel.

2. The method according to claim 1, in which the compound is administered by oral, intravenous, intranasal, sublingual or rectal administration.

3. A method for inhibiting growth or proliferation of melanoma cells in an individual, wherein the method comprises administering, to the individual, a compound having the structure:

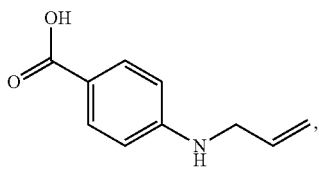

or a pharmaceutically acceptable salt thereof, in an amount effective to inhibit growth or proliferation of the tumor cells.

4. The method according to claim 3, in which the compound is administered in combination with a chemotherapeutic compound.

5. The method according to claim 4, in which the chemotherapeutic compound is paclitaxel.

6. The method according to claim 3, in which the compound is administered in combination with ionizing radiation.

7. The method according to claim 3, in which the compound is administered by oral, intravenous, intranasal, sublingual or rectal administration.

* * * * *